(12) United States Patent
Jung et al.

(10) Patent No.: US 8,874,381 B2
(45) Date of Patent: Oct. 28, 2014

(54) METHOD OF MEASURING DESTRUCTION RATE OF REFRIGERANT

(75) Inventors: Dae Sung Jung, Incheon (KR); Jun Young Lee, Seoul (KR); Jong Rae Cho, Gyeonggi-do (KR); Han Seok Kim, Seoul (KR)

(73) Assignee: Hyundai Motor Company, Seoul (KR)

(*) Notice: Subject to any disclaimer, the term of this patent is extended or adjusted under 35 U.S.C. 154(b) by 711 days.

(21) Appl. No.: 13/172,012

(22) Filed: Jun. 29, 2011

(65) Prior Publication Data

US 2012/0253690 A1 Oct. 4, 2012

(30) Foreign Application Priority Data

Mar. 29, 2011 (KR) .................. 10-2011-0028422

(51) Int. Cl.
| | | |
|---|---|---|
| *G01N 1/22* | (2006.01) | |
| *G01N 30/88* | (2006.01) | |
| *G06F 17/40* | (2006.01) | |
| *G06F 19/00* | (2011.01) | |
| *G01N 30/72* | (2006.01) | |

(52) U.S. Cl.
CPC ............ *G01N 31/8606* (2013.01); *G06F 17/40* (2013.01); *G01N 1/2258* (2013.01); *G06F 19/00* (2013.01); *G01N 30/7206* (2013.01); *G01N 30/88* (2013.01); *G01N 2030/8845* (2013.01)
USPC ................ 702/24; 62/125; 62/529; 73/64.56; 702/1; 702/127; 702/182; 702/187; 702/189

(58) Field of Classification Search
CPC ........... G01D 7/00; G01D 9/00; G01D 21/00; G01M 15/00; G01M 15/04; G01M 15/10; G01M 15/102; G01M 99/00; G01N 1/00; G01N 1/02; G01N 1/22; G01N 1/2247; G01N 1/2258; G01N 30/00; G01N 30/02; G01N 30/62; G01N 30/72; G01N 30/7206; G01N 30/86; G01N 30/88; G01N 2030/00; G01N 2030/02; G01N 2030/88; G06F 11/00; G06F 11/30; G06F 11/32; G06F 11/34; G06F 17/00; G06F 17/40; G06F 19/00
USPC ............... 62/125, 529; 73/23.2, 53.01, 64.54, 73/64.56, 865.8, 866.3; 702/1, 22, 23, 24, 702/127, 182, 187, 189; 708/100, 105, 200
See application file for complete search history.

(56) References Cited

U.S. PATENT DOCUMENTS

| | | | | | |
|---|---|---|---|---|---|
| 2,618,132 | A | * | 11/1952 | Pottenger, Jr. ................ | 62/470 |
| 2,955,252 | A | * | 10/1960 | Williams ...................... | 324/307 |
| 3,005,911 | A | * | 10/1961 | Burhans ........................ | 250/281 |
| 3,359,784 | A | * | 12/1967 | Jorre et al. .................... | 73/23.2 |
| 3,520,657 | A | * | 7/1970 | Frumerman .................... | 436/56 |

FOREIGN PATENT DOCUMENTS

| | | |
|---|---|---|
| JP | 10-153591 | 6/1998 |
| JP | 2000-065797 | 3/2000 |
| JP | 2001-013122 | 1/2001 |
| JP | 2001-050944 | 2/2001 |
| KR | 10-0829500 B1 | 5/2008 |
| KR | 10 2008 0059366 | 6/2008 |

* cited by examiner

*Primary Examiner* — Edward Cosimano
(74) *Attorney, Agent, or Firm* — Edwards Wildman Palmer LLP; Peter F. Corless

(57) ABSTRACT

The present invention provides a method for calculating a destruction rate of refrigerant by establishing a calibration line using standard refrigerant gases and measuring the amount of refrigerant remaining in exhaust gas discharged after destruction of waste refrigerant. For this purpose, the present invention provides a method for calculating a destruction rate of refrigerant, the method including: establishing a calibration line using standard refrigerant gas samples whose concentrations are known; sampling exhaust gas finally discharged after decomposition of waste refrigerant; measuring the concentration of refrigerant remaining in the sampled exhaust gas; and calculating the amount of undestroyed refrigerant using the concentration of refrigerant remaining in the exhaust gas, the amount of exhaust gas discharged, and the known density of refrigerant.

13 Claims, 7 Drawing Sheets

US 8,874,381 B2

METHOD OF MEASURING DESTRUCTION RATE OF REFRIGERANT

CROSS-REFERENCE TO RELATED APPLICATION

This application claims under 35 U.S.C. §119(a) the benefit of Korean Patent Application No. 10-2011-0028422 filed Mar. 29, 2011, the entire contents of which are incorporated herein by reference.

BACKGROUND (a) Technical Field

The present invention relates to a method for calculating a destruction rate of refrigerant. More particularly, it relates to a method for calculating a destruction rate of refrigerant by establishing a calibration line using standard refrigerant gases and measuring the amount of refrigerant remaining in exhaust gas discharged after destruction of waste refrigerant.

(b) Background Art

At present, waste refrigerant produced during collection, recovery, and disposal is released into the atmosphere without any proper treatment, and most waste refrigerant typically contains chlorofluorocarbon (CFC), an ozone-depleting substance, and hydrofluorocarbon (HFC), which is a global warming substance.

In certain countries, such as Korea, there is no facility that can properly treat and destroy the waste refrigerant used in vehicles, household appliances, industrial appliances, etc. Moreover, a method and apparatus that can measure the amount of undestroyed refrigerant remaining in exhaust gas after destruction of waste refrigerant has not been provided, and thus it is not possible to become informed on the destruction rate of refrigerant.

As examples, under the Montreal Protocol that regulates ozone-depleting substances, the destruction rate of CFC is defined as 99.99% or higher. Also, in Japan, in the case of smokestack facilities, the destruction rate is 99% or higher and the amount of CFC in exhaust gas is 1 ppm or lower, while in the case of other facilities, the destruction rate is 99.9% or higher and the amount of CFC in exhaust gas is 15 ppm or lower. Further, in Korea, the "Act on the Resource Circulation of Electrical and Electronic Equipment and Vehicles" has been put into effect in 2008, and the standards on the destruction rate with respect to the treatment of waste refrigerant have been established.

Therefore, a monitoring method and apparatus for measuring the amount of refrigerant remaining in exhaust gas after destruction at sub-ppm levels is required.

The above information disclosed in this Background section is only for enhancement of understanding of the background of the invention and therefore it may contain information that does not form the prior art that is already known to a person of ordinary skill in the art.

SUMMARY OF THE DISCLOSURE

The present invention provides a method for calculating a destruction rate of refrigerant by establishing a calibration line using standard refrigerant gas samples, measuring the amount of refrigerant remaining in exhaust gas from the established calibration line to calculate the amount of undestroyed refrigerant, and determining the decomposition level of refrigerant using the calculated value.

In one aspect, the present invention provides method for calculating a destruction rate of refrigerant, the method comprising: establishing a calibration line using standard refrigerant gas samples whose concentrations are known; sampling exhaust gas finally discharged after decomposition of waste refrigerant; measuring the concentration of refrigerant remaining in the sampled exhaust gas; and calculating the amount of undestroyed refrigerant using the concentration of refrigerant remaining in the exhaust gas, the amount of exhaust gas discharged, and the known density of refrigerant.

In a preferred embodiment, the sampled exhausted gas is fed into a first cooling chamber at $-2°$ C. to reduce water content, fed into a second cooling chamber at $-15°$ C. to further reduce water content, discharged at room temperature, and then passes through a water trap to remove a very small amount of the remaining water.

In another preferred embodiment, the calibration line is established by taking the concentration of refrigerant on the vertical axis and a peak area of refrigerant on the horizontal axis.

In still another preferred embodiment, in the measuring of the concentration of refrigerant remaining in the exhaust gas, the concentration of refrigerant remaining in the exhaust gas is calculated from the calibration line by measuring the peak area of refrigerant remaining in the exhaust gas using gas chromatograph/mass spectroscope (GC/MS).

Other aspects and preferred embodiments of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
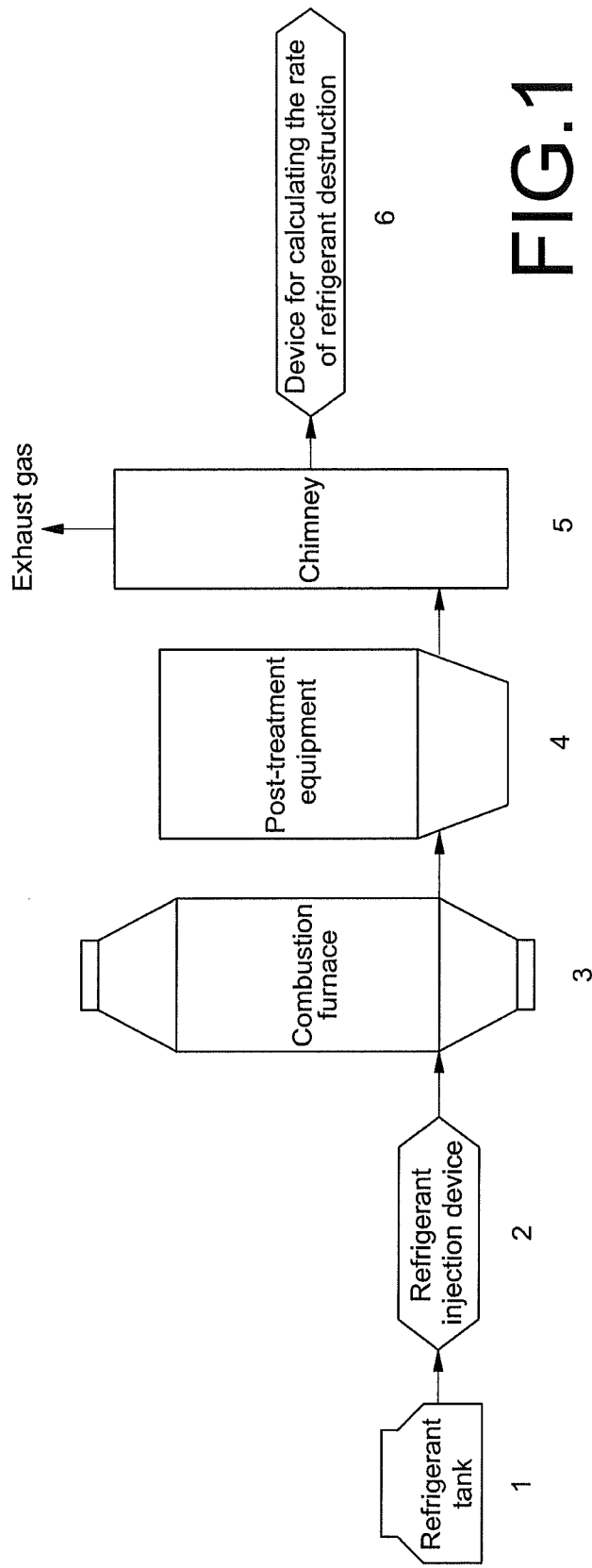
FIG. 1 is a diagram showing the configuration of a refrigerant treatment facility.

Reference numerals set forth in the Drawings includes reference to the following elements as further discussed below:

1: refrigerant tank;
2: refrigerant injection device;
3: combustion furnace;
4: post-treatment equipment;
5: chimney;
6: device for calculating the rate of refrigerant destruction;
10: standard gas sampling device;

12: standard gas tank;
20: exhaust gas sampling device;
21: exhaust gas bypass line;
22: pump;
24: first cooler;
25: second cooler;
26: water trap;
28: dust filter;
30: device for analyzing the amount of undestroyed refrigerant;
32: mass flow controller (MFC);
34: gas chromatograph (GC);
36: mass spectroscope (MS); and
50: porous layer open tubular (PLOT) column.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

Also, it is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The present invention provides a method for calculating a destruction rate of refrigerant by measuring the concentration of refrigerant in exhaust gas discharged after destruction of waste refrigerant to calculate the amount of undestroyed refrigerant and determining the destruction rate of refrigerant to be analyzed.

As show in FIG. 1, waste refrigerant (from tank 1) is injected through a refrigerant injection device 2 into a combustion furnace 3 to be decomposed in the combustion furnace at 850° C. for two seconds or longer, subjected to post-treatment equipment 4 to remove harmful gases, and finally discharged through a chimney 5.

To identify the decomposition level of refrigerant, it is necessary to measure the destruction rate of refrigerant, and related formulas are as follows:

Destruction rate of refrigerant=[1−(Amount of undestroyed refrigerant)/(Amount of injected refrigerant)*100]

Amount of undestroyed refrigerant=Concentration of refrigerant in exhaust gas*Amount of exhaust gas*Density of refrigerant The amount of injected refrigerant can be measured by a flowmeter or load cell in the refrigerant injection device. In the case of a typical combustion furnace, the amount of exhaust gas is measured in real time, and the density of refrigerant can be found in the literatures as well known in the art. Therefore, to calculate the amount of undestroyed refrigerant, it is necessary to measure the concentration of refrigerant in exhaust gas.

The present invention aims at measuring the destruction rate of refrigerant (generally, by device "6") based on a peak area by comparing a standard refrigerant gas and a refrigerant remaining in exhaust gas at sub-ppm levels using gas chromatography/mass spectroscope (GC/MS).

Figure 2:
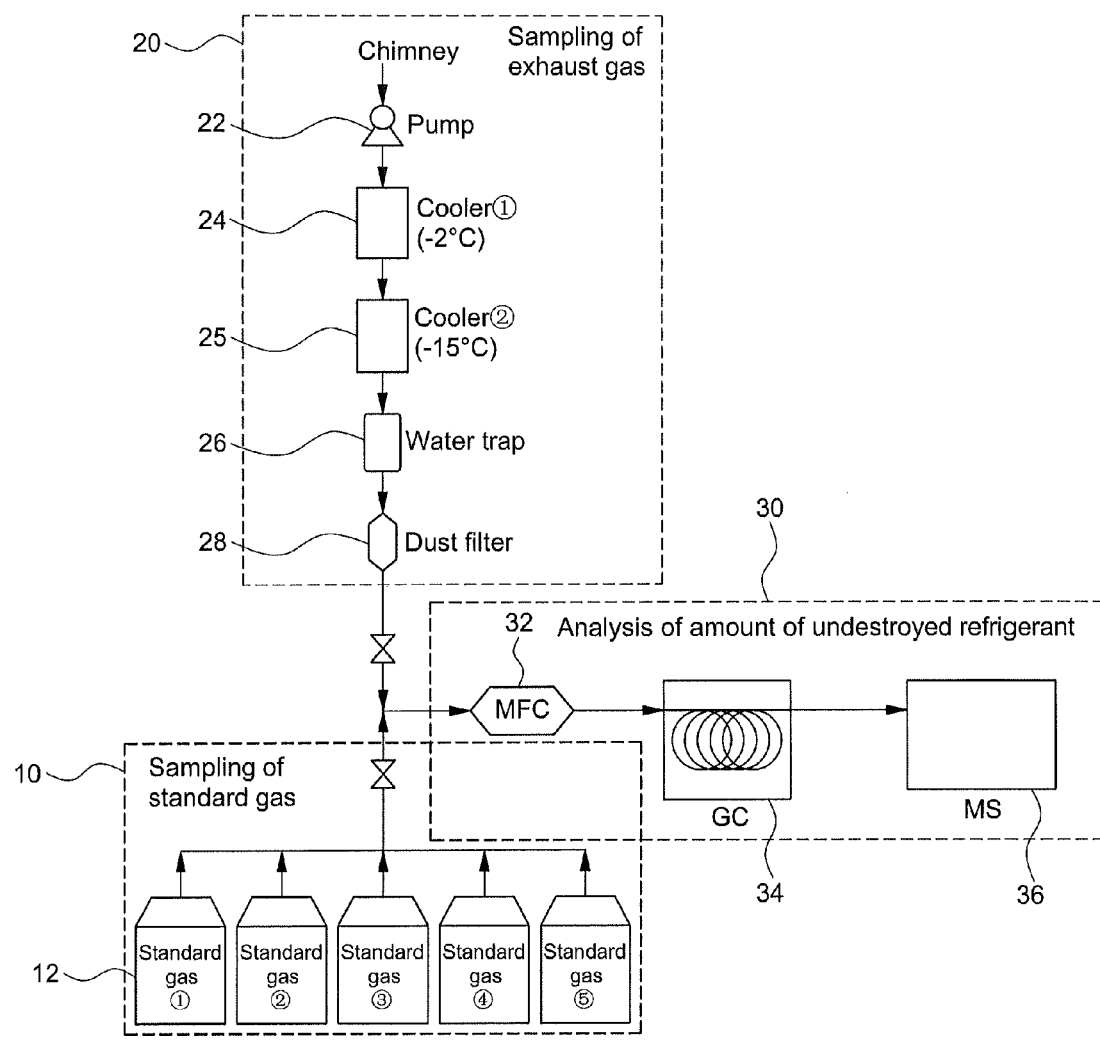
FIG. 2 is a diagram showing the configuration of a system for measuring the destruction rate of refrigerant in accordance with an illustrative embodiment of the present invention.

As shown in FIG. 2, a system for measuring the destruction rate of refrigerant according to the present invention (e.g., device 6 of FIG. 1) generally includes a standard gas sampling device 10, an exhaust gas sampling device 20, and a device 30 for analyzing the amount of undestroyed refrigerant.

Figure 3:
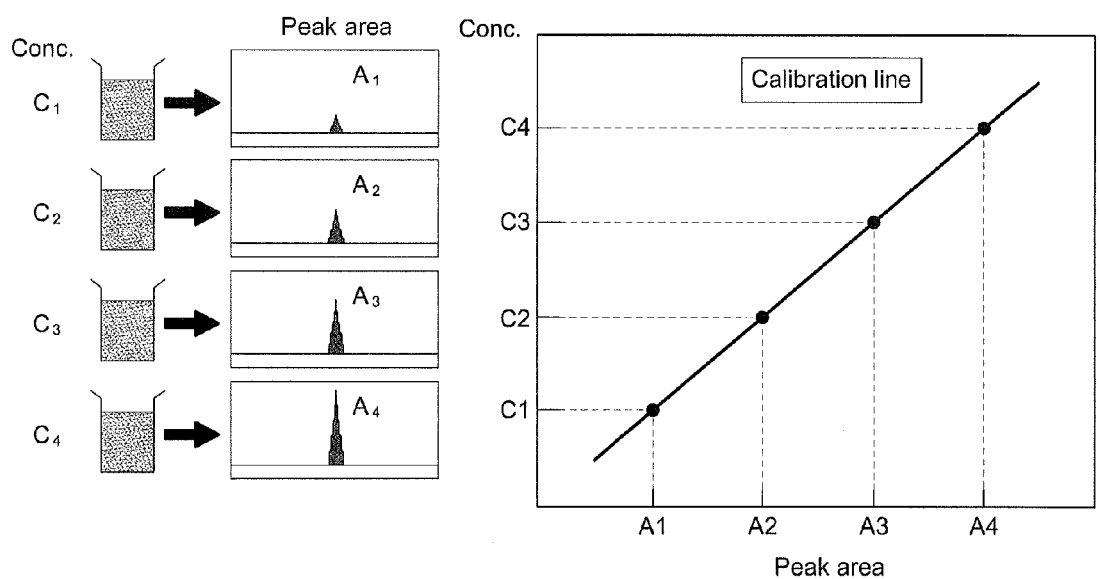
FIG. 3 is a diagram showing a calibration line established in accordance with an illustrative embodiment of the present invention.

First, the standard gas sampling device 10 includes standard gas tanks 12, into which illustratively at least four types of gases whose concentrations are known are injected, to establish a calibration line. FIG. 3 is an exemplary diagram schematically showing a process of establishing a calibration line and an established calibration line according to the present invention.

The calibration line is established in the following manner. The standard gases of refrigerant to be analyzed are prepared at illustratively four to five concentrations ($C_1$-$C_4$), and a predetermined amount of each standard gas is introduced into the GC/MS (34/36) to perform analysis. The concentration (or absolute quantity) of refrigerant among the introduced standard refrigerant gas samples is plotted on the vertical axis and its peak area (height, $A_1$-$A_4$, respectively) is plotted on the horizontal axis, thus establishing a calibration line.

In other words, after the analysis using the GC/MS, a graph is plotted by taking the concentration of each standard gas on the vertical axis and the peak area on the horizontal axis, and the plotted graph is used as a calibration line of the refrigerant to be analyzed.

After the calibration line is established as shown in FIG. 3, the same amount of a subject sample (of refrigerant to be analyzed) as the standard gas is introduced under the same conditions to estimate the concentration of the refrigerant to be analyzed (on the vertical axis) from the peak area (on the horizontal axis) of the subject sample using the calibration line.

That is, the same amount of refrigerant to be analyzed as the standard gas is introduced into the GC/MS to measure a peak area, and the measured peak area is substituted into the calibration line, thereby determining the concentration of the refrigerant to be analyzed.

Second, to measure the amount of refrigerant in exhaust gas, the exhaust gas sampling device 20 functions to sample exhaust gas finally discharged through a chimney 5 after waste refrigerant injected into the combustion furnace 3 is decomposed and subjected to the post-treatment equipment 4 to remove harmful gases.

Figure 4:
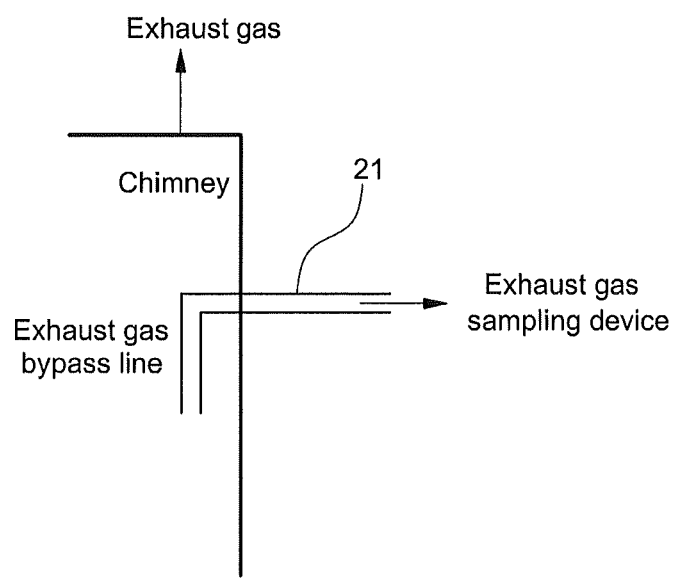
FIG. 4 is a schematic diagram showing a process of sampling exhaust gas discharged after destruction of waste refrigerant in accordance with an illustrative embodiment of the present invention.

As shown in FIG. 4, a predetermined amount of exhaust gas produced from the combustion furnace is sampled through a bent pipe (i.e., an exhaust gas bypass line 21) and supplied to the exhaust gas sampling device 20.

Referring to FIGS. 2 and 4, the exhaust gas sampling device 20 samples the exhaust gas from the bypass line in the chimney through a pump 22 and supplies the sampled exhaust gas to the device 30 for analyzing the amount of undestroyed refrigerant via a first cooler 24, a second cooler 25, a water trap 26, and a dust filter 28, through which water and dust are removed.

Typically, the exhaust gas discharged from the combustion furnace has a water content of 5 to 20% and a temperature of 100° C. or higher, and thus a gas at room temperature, from which water is removed, is required for the analysis in the GC/MS.

The exhaust gas discharged from the combustion furnace is fed into a cooling chamber (i.e., the first cooler 24) maintained at −2° C. to condense water and is discharged, thus the water content can be reduced to a sub-percent level.

The exhaust gas from which water is first removed is then fed into a cooling chamber (i.e., the second cooler 25) maintained at up to −15° C. to further reduce water content and is discharged at room temperature, thus the water content can be reduced to a sub-ppm level.

The resulting exhaust gas from which water is further removed is then passed through the water trap 26 (e.g., a chemical trap using silica, alumina, etc.) to remove a very small amount of the remaining water, and the water trap 26 serves as an indication with which the removal of water and the filter durability can be identified.

Here, the temperature of the second cooler 25 is set to −15° C. considering that the boiling point of the refrigerant is generally −20 to −30° C. (for example, the boiling point of HFC-134a is −26° C. and that of CFC-12 is −30° C.) and in view of the properties of condensable gas changing from gaseous phase to liquid phase.

Third, the device 30 for analyzing the amount of undestroyed refrigerant includes a mass flow controller (MFC) 32, a gas chromatograph (GC) 34, and a mass spectroscope (MS) 36.

The MFC 32 controls the flow rates of the standard gas and the exhaust gas under a constant rate and injects the resulting gases to the device 30, in which the controlled flow rate ranges from 0 to 500 ccm and the controlled pressure ranges from 0 to 3 kgf/cm$^2$.

Figure 5:
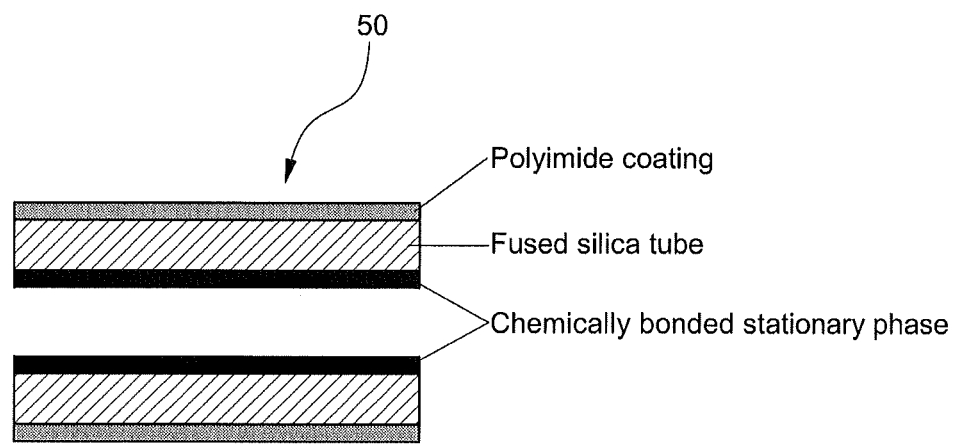
FIG. 5 is a diagram showing a porous layer open tubular (PLOT) column used in the present invention.

The GC 34 allows a qualitative analysis by separating a specific gas from a gas mixture at different time points using a column. As shown in FIG. 5, a porous layer open tubular (PLOT) column 50 is used to facilitate the gas separation.

The MS 36 is a device used to accurately measure the mass using the properties that the accelerated ions are deflected by electric field or magnetic field, and measures the concentration of refrigerant in exhaust gas using a selective ion monitoring (SIM) mode.

Next, a process of calculating the destruction rate of waste refrigerant according to the method for measuring the destruction rate of refrigerant will be described in detail, but the present invention is not limited thereto.

A waste treatment gasification melting furnace was used as the combustion furnace, in which the flow rate of HFC-134a was 3 kg/hr and the flow rate of exhaust gas was 30,000 m$^3$/hr.

Figure 6:
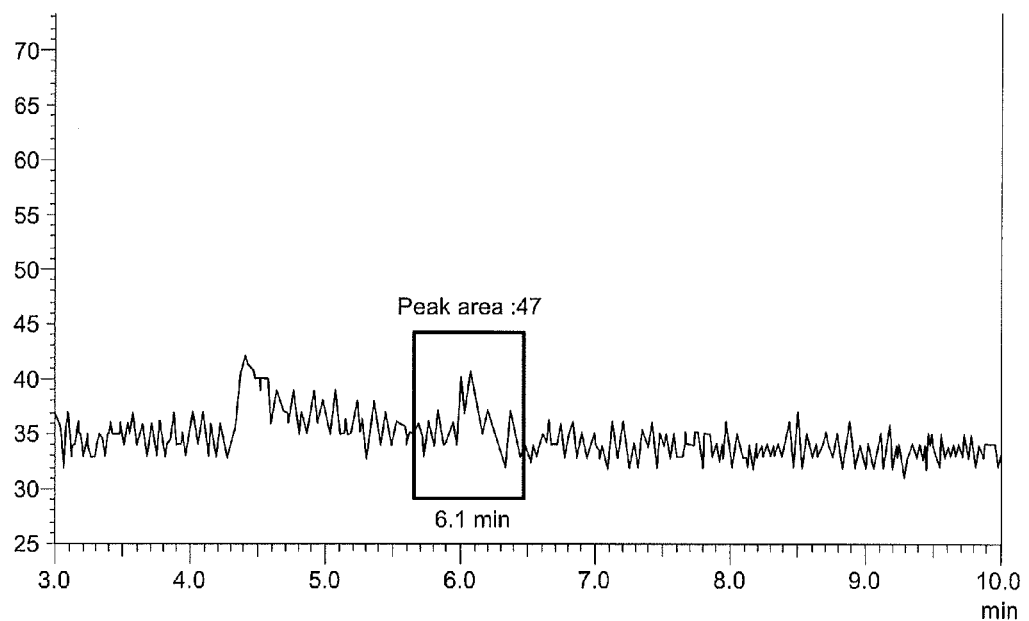
FIG. 6 is a diagram showing the analysis results of the concentration of undestroyed refrigerant in exhaust gas after destruction of HFC-134a refrigerant in accordance with an illustrative embodiment of the present invention.

Table 1 and FIG. 6 show the results of the concentration of HFC-134a standard gas, a refrigerant mainly used in vehicles and refrigerators, and the concentration of undestroyed refrigerant in exhaust gas after destruction of waste refrigerant.

TABLE 1

| Classification | Concentration | Peak area by GC/MS analysis |
|---|---|---|
| HFC-134a standard gas | 1,000 ppb | 81,419 |
| HFC-134a standard gas | 100 ppb | 8,096 |
| HFC-134a standard gas | 10 ppb | 969 |
| HFC-134a standard gas | 1 ppb | 140 |
| Exhaust gas after refrigerant destruction | 0.6 ppb | 47 |

Figure 7:
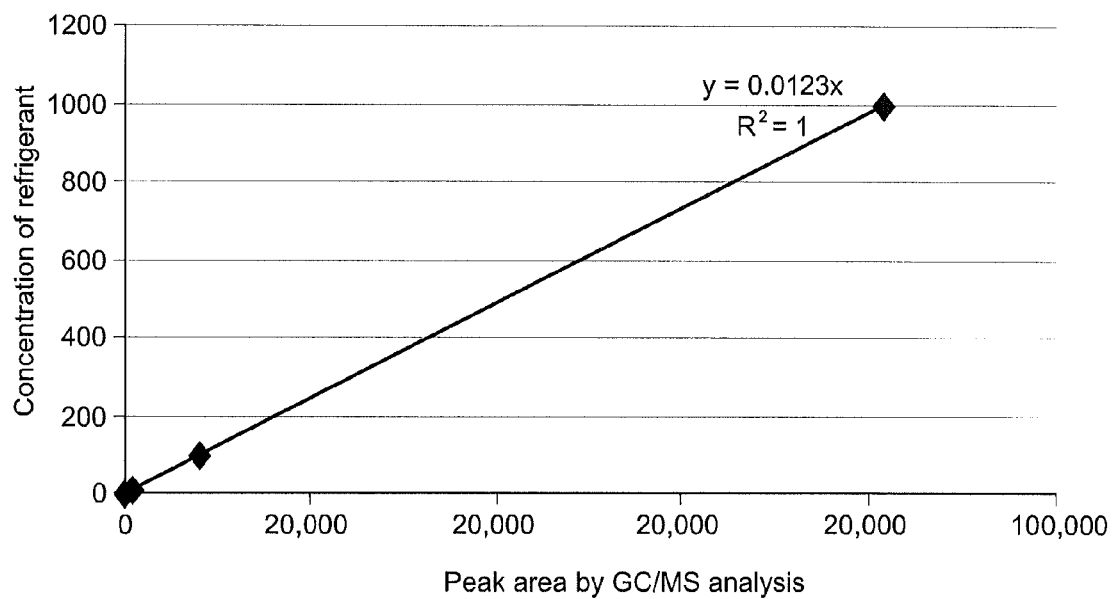
FIG. 7 is a diagram showing a calibration line of HFC-134a refrigerant established in accordance with an illustrative embodiment of the present invention.

As shown in Table 1, HFC-134a standard gas at a concentration of 1 ppb, 10 ppb, 100 ppb, and 1,000 ppb, respectively, was prepared, and a predetermined amount of each standard gas was introduced into the GC 34 and the MS 36 to perform analysis, and a calibration line was established as shown in FIG. 7.

Here, the concentration (or absolute quantity) of HFC-134a to be analyzed in the introduced standard gas was plotted on the vertical axis, and the peak area obtained by the GC/MS analysis was plotted on the horizontal axis.

After the calibration was established, the concentration of HFC-134a, 0.6 ppb, was calculated from the peak area, 47, obtained by analyzing the exhaust gas after destruction of refrigerant under the same conditions.

Then, the destruction rate of refrigerant was calculated by the following formulas. As a result, the destruction rate of refrigerant was 99.997% (which, notably, satisfied both the Montreal Protocol and the Japanese regulations).

$$\begin{aligned}
\text{Amount of undestroyed refrigerant} &= \text{Concentration of refrigerant in exhaust gas } * \\
&= \text{Amount of exhaust gas } * \text{ Density of refrigerant} \\
&= 0.6 \text{ ppb } * \; 30,000 \text{ m}^3/\text{hr } * \; 4.25 \text{ kg/m}^3 \\
&= 0.0000765 \text{ kg/hr}
\end{aligned}$$

$$\begin{aligned}
\text{Destruction rate of refrigerant} &= [1 - (\text{Amount of undestroyed refrigerant})/ \\
&= (\text{Amount of injected refrigerant}) \; * \; 100] \\
&= [1 - (0.0000765 \text{ kg/hr})/(3 \text{ kg/hr}) \; * \; 100 \\
&= 99.997\%
\end{aligned}$$

As such, according to the present invention, the destruction rate of waste refrigerant can be calculated by quantitative analysis.

As described above, the method for measuring the destruction rate of refrigerant according to the present invention can provide the following effects:

1. It is possible to comply with the Montreal Protocol and future regulations on the destruction rate of refrigerant;
2. The method of the present invention can be applied to waste incineration facilities such as household waste and industrial waste as well as dedicated treatment facilities for refrigerant destruction;
3. With the quantification of the destruction rate of refrigerant, it is possible to determine optimal operation conditions by controlling refrigerant destruction operation conditions such as the temperature, retention time, vapor, etc. in the combustion furnace; and
4. It is possible to achieve greenhouse gas reduction by real-time monitoring of the destruction rate of refrigerant.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A method for calculating a destruction rate of refrigerant, the method comprising:
    establishing a calibration line using standard refrigerant gas samples whose concentrations are known;
    measuring and sampling an amount of exhaust gas finally discharged after decomposition of waste refrigerant;
    measuring the concentration of refrigerant remaining in the sampled exhaust gas using the established calibration line; and
    calculating the amount of undestroyed refrigerant using the concentration of refrigerant remaining in the exhaust gas, the amount of exhaust gas discharged, and a known density of refrigerant.

2. The method of claim 1, wherein sampling the exhaust gas comprises:
    feeding the exhaust gas into a first cooling chamber at −2° C. to reduce water content;
    feeding the exhaust gas into a second cooling chamber at −15° C. to further reduce water content;
    discharging the exhaust gas at room temperature; and then passing the exhaust gas through a water trap to remove a very small amount of the remaining water.

3. The method of claim 1, wherein the calibration line is established by taking the concentration of refrigerant on the vertical axis and a peak area of refrigerant on the horizontal axis.

4. The method of claim 1, wherein, in the measuring of the concentration of refrigerant remaining in the exhaust gas, the concentration of refrigerant remaining in the exhaust gas is calculated from the calibration line by measuring a peak area of refrigerant remaining in the exhaust gas using gas chromatography/mass spectroscope (GC/MS).

5. The method of claim 1, wherein the refrigerant is a hydrofluorocarbon (HFC).

6. The method of claim 5, wherein the refrigerant is HFC-134a.

7. A system for calculating a destruction rate of refrigerant, the system comprising:
    a standard gas sampling device configured to sample a plurality of standard refrigerant gas samples whose concentrations are known;
    an exhaust gas sampling device configured to measure and sample an amount of exhaust gas finally discharged after decomposition of waste refrigerant; and
    a device configured to:
    a) establish a calibration line using the standard refrigerant gas samples whose concentrations are known;
    b) measure the concentration of refrigerant remaining in the sampled exhaust gas using the established calibration line; and
    c) calculate the amount of undestroyed refrigerant using the concentration of refrigerant remaining in the exhaust gas, the amount of exhaust gas discharged, and a known density of refrigerant.

8. The system of claim 7, wherein the exhaust gas sampling device comprises:
    a first cooling chamber to which the exhaust gas is fed, the first cooling chamber at −2° C. to reduce water content;
    a second cooling chamber to which the exhaust gas is fed, the second cooling chamber at −15° C. to further reduce water content; and
    a water trap configured to receive the exhaust gas discharged from the second cooling chamber at room temperature, and then to remove a very small amount of the remaining water from the exhaust gas.

9. The system of claim 7, wherein the device is configured to establish the calibration line by taking the concentration of refrigerant on the vertical axis and a peak area of refrigerant on the horizontal axis.

10. The system of claim 7, wherein the device is configured to measure the concentration of refrigerant remaining in the exhaust gas through a calculation from the calibration line by measuring a peak area of refrigerant remaining in the exhaust gas using gas chromatography/mass spectroscope (GC/MS).

11. The system of claim 7, wherein the refrigerant is a hydrofluorocarbon (HFC).

12. The system of claim 11, wherein the refrigerant is HFC-134a.

13. A system for calculating a destruction rate of refrigerant, the system comprising:
    means for establishing a calibration line using standard refrigerant gas samples whose concentrations are known;
    means for measuring and sampling an amount of exhaust gas finally discharged after decomposition of waste refrigerant;
    means for measuring the concentration of refrigerant remaining in the sampled exhaust gas using the established calibration line; and
    means for calculating the amount of undestroyed refrigerant using the concentration of refrigerant remaining in the exhaust gas, the amount of exhaust gas discharged, and a known density of refrigerant.

* * * * *